United States Patent [19]

Quirk et al.

[11] Patent Number: 4,780,554
[45] Date of Patent: Oct. 25, 1988

[54] O-SILYLATED KETENE ACETALS AND ENOL ETHERS AND METHOD OF PREPARATION

[75] Inventors: Jennifer M. Quirk, Bedford Hills; Linda K. Kozak, Ossining; Bernard Kanner, West Nyack, all of N.Y.

[73] Assignee: Union Carbide Corporation, Danbury, Conn.

[21] Appl. No.: 741,832

[22] Filed: Jun. 6, 1985

Related U.S. Application Data

[63] Continuation-in-part of Ser. No. 673,285, Nov. 20, 1984, abandoned.

[51] Int. Cl.$^4$ .................. C07F 7/08; C07F 7/10; C07F 7/18
[52] U.S. Cl. .................... 556/410; 556/446; 556/453; 556/456; 556/457; 556/482; 556/483; 556/460; 556/461
[58] Field of Search .............. 556/410, 446, 453, 456, 556/457, 482, 483, 460, 461

[56] References Cited

U.S. PATENT DOCUMENTS

| | | | |
|---|---|---|---|
| 4,294,975 | 10/1981 | Takago et al. | 556/482 |
| 4,414,372 | 11/1983 | Farnham et al. | 526/190 |
| 4,417,034 | 11/1983 | Webster | 526/190 |

FOREIGN PATENT DOCUMENTS

| | | | |
|---|---|---|---|
| 68887 | 6/1981 | European Pat. Off. | 526/190 |

OTHER PUBLICATIONS

"New Way to Catalyze Polymerization" Science, 222 (4619), p. 39, Oct. 7, 1983.
"Reduction of Carbonyl Compounds Via Hydrosilylation" Journal of Organometallic Chemistry, 94 (1975) 449–461.
"Hydrosilylation of $\alpha,\beta$-Unsaturated Nitriles and Esters Catalyzed by Tris(Triphenylphosphine)Chlororhodium" Journal of Organometallic Chemistry, 111 (1976) 43–60.
"Hydrobilation of $\alpha,\beta$-Unsaturated Esters" Chem. Pharm. Bull. 22 (11) 2767–2769 (1974).
"Hydrosilylation of Dienes, Acetylenes and Carbonyls Catalyzed by Transition Metal Complexes" Sagami Chemical Research Center.
"Latest Research on the Hydrosilylation Reaction" Uspekhi Khimii, 46, 507–529 (1977).
"Reaction of 2-Alkyl-and 2-Aryl-1H, 3H-Organodisilazanes With Unsaturated Compounds", Izuestiya Adademii, No. 7, pp. 1539–1545 (1969).
"Synthesis of Modified Organocyclosilazanes" Zhurnal Obshchei Khimii, vol. 40, No. 5, pp. 1082–1088 (1970).
"Kinetics of the Addition of Unsaturated Compounds to Alkylhydrocyclosilazanes" Zhurnal Obshchei Khimii, vol. 38, No. 3, p. 655 (1968).
Reaction of 1,3-Dihydromethyldisilazanes and 1,3-Dihydro-Tetramethyldisiloxane with Allylamines" Izvestiya Akademii, No. 2, p. 351 (1968).
Chem. Abstracts, 86 155737v.

*Primary Examiner*—Paul F. Shaver
*Attorney, Agent, or Firm*—P. W. Leuzzi

[57] ABSTRACT

Novel O-silylated ketene acetals and enol ethers are prepared via the 1,4-hydrosilation of a hydrosilation composition selected from the group consisting of aminosilanes, siloxanes and alkylalkoxysilanes with an $\alpha,\beta$-unsaturated carbonyl in the presence of a rhodium catalyst.

24 Claims, No Drawings

O-SILYLATED KETENE ACETALS AND ENOL ETHERS AND METHOD OF PREPARATION

RELATED APPLICATIONS

This is a continuation-in-part application of U.S. Ser. No. 673,285 filed Nov. 20, 1984, now abandoned.

BACKGROUND OF THE INVENTION

The present invention generally relates to a novel class of O-silylated ketene acetals and enol ethers and a process for preparing the same. More specifically, the present invention is concerned with these O-silylated ketene acetals and enol ethers which are prepared via the 1,4 hydrosilation of a hydrosilation composition selected from the group consisting of aminosilanes, siloxanes and alkylalkoxysilanes with an α,β-unsaturated carbonyl compound.

THE PRIOR ART

In U.S. Pat. Nos. 4,417,034 and 4,414,372 it was reported that a variety of O-silylated ketene acetals have utility as initiators for group transfer polymerization. O-silylated ketene acetals and enol ethers can be prepared via several known synthetic routes, among which include hydrosilation.

The hydrosilation reaction was discovered in 1947 and over the years has become one of the best known and most widely practiced reactions in organosilicon chemistry, including its use in a wide variety of large scale commercial applications. It has also been the subject of several extensive reviews, see for instance: *Organic Insertion Reactions of Group II Elements*, Consultants Bureau, N.Y., 1966; *Organometallic Compounds of the Group IV Elements*, Dekker, N.Y., 1968, Vol. I; *Preparation of Carbofunctional Organosilanes by an Addition Reaction*, Moscow, 1971; Russ. Chem Rev., 46, 264 (1977); and J. Organometal Chem. Library 5, 1977, pg. 1–179.

In operating a hydrosilation reaction, various transition metals are known to be effective catalysts. U.S. Pat. No. 2,823,218 teaches chloroplatinic acid, a soluble form of platinum, as a particularly effective hydrosilation catalyst.

The prior art involving hydrosilations by aminosilanes is concentrated, in large measure, in a series of papers published between 1968–1970. Russian workers reported that disilazanes such as $HN(SiMe_2H)_2$ and cyclosilazanes such as $(HNMe_2H)_4$ underwent slow hydrosilation: Izv. Akad. Nauk SSSR, Ser. Khim. 1968, pg 351–6; and 1969, pg 1539–45; Zhur. Obshch. Khim. 38, 655, (1968); and 40, 1082, (1970). These reports were confirmed by workers at Dow Corning who went on to demonstrate that mono-, bis-, and tris-(dialkylamino)silanes showed no reactivity for hydrosilation J. Org. Chem. 35, 3879 (1970).

There appeared to be little hydrosilation potential for aminosilanes until a Russian paper disclosed reactions of hydrosilazanes with arylacetylenes, Soobshch Akad. Nauk Gruz. SSR, 84, 381 (1976), and, Tezisy Dokl-Vses. Konf. Khim. Atsetilena, 5th, 1975, 172.

Similarly, it was reported in the literature that triethylsilane undergoes a 1,4-hydrosilation with methacrylates using $RhCl(PPH_3)_3$ as a catalyst, Chem. Pharm. Bull. Japan, 22 (1974) 2767, and, J. Organomet. Chem. 111 (1976) 43. However, following these teachings a mixture of 1,4- and 1,2-hydrosilated products are formed when acrylates are employed in the reaction.

Despite this background of art there continued to exist a need for a one-step preparation of O-silylated ketene acetals and enol ethers which would primarily yield the 1,4-hydrosilated product. This need was significantly increased in view of the discovery that such materials may find utility as initiators in group transfer polymerization. The primary object of this invention was to provide a route to O-silylated ketene acetals and enol ethers as would yield the 1,4-hydrosilated product. Another object of the present invention was to arrive at new classes of O-silylated ketene acetals and enol ethers which may be useful as initiators in group transfer polymerization. Other objects of the invention will become apparent from the disclosure contained herein.

SUMMARY OF THE INVENTION

The present invention provides a novel class of O-silylated ketene acetals and enol ethers and a one-step method of preparing such O-silylated ketene acetals and enol ethers which primarily yields the 1,4-hydrosilated product. The novel O-silylated ketene acetals and enol ethers are those prepared via a 1,4-hydrosilation of a hydrosilation composition selected from the group consisting of aminosilanes, siloxanes, and alkylalkoxysilanes with an α,β-unsaturated carbonyl compound in the presence of a rhodium catalyst.

DETAILED DESCRIPTION OF THE INVENTION

In accordance with the present invention, there is provided a novel method of preparing O-silylated ketene acetals and enol ethers. The method comprises the 1,4-hydrosilation of a hydrosilation composition selected from the group consisting of aminosilanes, siloxanes and alkylalkoxysilanes with an α,β-unsaturated carbonyl compound.

Aminosilanes useful in the hydrosilation include those represented by the general formula:

$$H-Si(NRR^1)_x(R^2)_{3-x} \qquad (I)$$

wherein R, $R^1$ and $R^2$ are individually alkyl or aryl groups containing from 1 to 8 carbon atoms R may also be hydrogen and wherein x has a value of 1, 2 or 3. These aminosilanes may be purchased commercially or prepared from any of a variety of known techniques, such as described in Eaborn, *Organosilicon Compounds*, Academic Press Inc., New York, 1690, p. 339.

Suitable aminosilanes include, but are not limited to, dimethylaminodimethylsilane, bis(dimethylamino)methylsilane, tris(dimethylamino)silane, dimethylaminomethylethylsilane, diethylaminomethylpropylsilane, methylaminomethylethylsilane, ethylaminomethylethylsilane, phenylaminomethylethylsilane, diphenylaminomethylphenylsilane, dibenzylaminoethylphenylsilane, diphenylaminodimethylsilane, bis(diethylamino)ethylsilane, bis(methylamino)ethylsilane, bis(benzylamino)methylsilane, tris(diethylamino)silane, tris(piperidino)silane, tris(cyclohexylamino)silane. Preferably the aminosilane is such that R, $R^1$ and $R^2$ are either methyl, ethyl or phenyl and x has a value of 3. Preferably the silane is tris(dimethylamino)silane.

Siloxanes useful in the hydrosilation include those represented by the general formula:

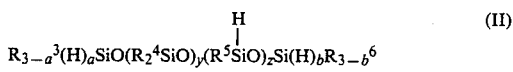

where in $R^3$, $R^4$, $R^5$ and $R^6$ are individually alkyl groups containing from 1 to 8 carbon atoms, and a has a value of 0 or 1, b has a value of 0 or 1, y has a value from 1 to 500, z has a value from 0 to 499, and, the sum of y+z equals from 1 to 500 with the proviso that if z is 0, a+b must equal at least one. The siloxanes may be purchased commercially or prepared from any of a variety of known techniques, such as described in Eaborn, *Organosilicon Compounds*, Academic Press Inc, New York, 1960, p. 228.

Suitable siloxanes include, but are not limited to, bis(trimethylsilyloxy)methylsilane 1,1,3,3-tetramethyldisiloxane, and heptamethylcyclotetrasiloxane. Most other siloxanes are mixtures of all types of siloxanes. Preferably the siloxane is such that $R^3$, $R^4$, $R^5$, $R^6$ are all methyl groups.

Alkylalkoxysilanes useful in the hydrosilation include those represented by the general formula set forth below:

wherein $R^7$ and $R^{10}$ may be the same or different throughout the silane and are individually an alkyl group containing from 1 to 8 carbon atoms and v is 0, or 1 or 2. The alkylalkoxysilanes may be purchased commercially or prepared by a variety of known techniques such as are described for example in U.S. Pat. No. 4,395,564. It is preferred that the alkylalkoxysilanes be prepared from secondary or tertiary alcohols and v is 0.

Suitable alkylalkoxysilanes include, but are not limited, triisopropoxysilane, trisecbutoxysilane, tritertbutoxysilane, triethoxysilane, trimethoxysilane, methyldiethoxysilane, dimethylethoxysilane, methyldiisopropoxysilane, dimethyltertbutoxysilane, methyldisecbutoxysilane, and dimethylmethoxysilane.

The α,β-unsaturated monomers the hydrosilation is run with is represented by the general formula:

wherein $R^8$ can be hydrogen or an alkyl or aryl group having from one to eight carbon atoms and Z is selected from the group consisting of hydrogen, an alkyl group, an aryl group, an alkoxy group and an aryloxy group containing from one to fifteen carbon atoms, preferably from one to eight carbon atoms. The α,β-unsaturated carbonyl compound such as acrylates or methacrylates can be purchased commercially or may be prepared by any of a variety of known techniques.

α,β-unsaturated carbonyls which are suitable for use in the practice of this invention are, in general, known compounds and include, but are not limited to, the following: methyl methacrylate; butyl methacrylate; lauryl methacrylate; ethyl acrylate; butyl acrylate; 2-ethylhexyl methacrylate; 2-(dimethylamino)ethyl methacrylate; 2-(dimethylamino)ethyl acrylate; 3,3-dimethoxypropyl acrylate; 3-methacryloxypropyl acrylate; 2-acetoxyethyl methacrylate; p-tolyl methacrylate; 2,2,3,3,4,4,4-heptafluorobutyl acrylate; ethyl 2-cyanoacrylate; N,N-dimethyl acrylamide; ethyl 2-cyanoacrylate; 4-fluorophenyl acrylate; 2-methylacryloxyethyl acrylate and linoleate; propyl vinyl ketone; methyl vinyl ketone; phenyl vinyl ketone; ethyl vinyl ketone; acrolein, methacrolein; ethyl 2-chloroacrylate; glycidyl methacrylate; 3-methoxypropyl methacrylate; 2-[(1-propenyl)oxy]ethyl methacrylate and acrylate; phenyl acrylate; 2-(trimethylsiloxy)ethyl methacrylate; and allyl acrylate and methacrylate. Preferred monomers include methyl methacrylate; glycidyl methacrylate; ethyl acrylate; butyl acrylate; 2-(trimethylsiloxy)ethyl methacrylate; 2-methacryloxyethyl acrylate; 2-acetoxyethyl methacrylate; and 2-(dimethylamino)ethyl methacrylate. Methyl methacrylate is most preferred.

To obtain primarily (more than 50% and usually more than 75%) the 1,4-hydrosilation product the hydrosilation reaction takes place in the presence of a rhodium catalyst. The rhodium catalyst may be used neat; on a support such as carbon black or alumina; or in a solvent as a soluble compound of rhodium, i.e. as rhodium trichloride, rhodium (III) 2,4-pentanedionate and complexes of rhodium with phosphines, such as tris(triphenylphosphine)rhodium chloride and tris(triphenylphosphine)rhodium carbonyl hydride. The rhodium catalyst is available commercially from Johnson Mathey. The concentration of the catalyst is normally between 0.000010–0.05 mole% with respect to the hydrosilation composition, it is preferred to use no more catalyst than required to obtain the necessary reaction due to the significant costs associated with catalysts of this type. However, impurities common in many α,β-unsaturated carbonyl compounds may necessitate higher concentrations.

The hydrosilation should be run at temperatures greater than 40° C. with the optimum being between 70° C. and 150° C. Although the upper temperature limit is not critical, the reaction should be below the decomposition point of the starting materials or products. The hydrosilation reaction may be carried out with or without solvent. In most cases there is no advantage to using a solvent. However, in cases where a solvent is desirable for reasons such as solubility or temperature control, a solvent may be used. Suitable solvents are hydrocarbons such as octane, xylene or triisopropylbenzene.

The order of addition of the reactants is not important, although normally, the rhodium catalyst is added to the hydrosilation composition, then heat is applied, followed by the addition of the α,β-unsaturated carbonyl compound. A stoichiometric ratio of one-to-one for the hydrosilation composition to the α,β-unsaturated carbonyl compound is preferred, although it is possible to alter this ratio slightly without adversely affecting the reaction. Any such change will, however, affect the reaction's yield.

The O-silylated ketene acetal or enol ether which the 1,4-hydrosilation produces is represented by the following general formulae:

A. When the hydrosilation composition is an aminosilane:

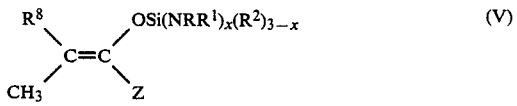

B. When the hydrosilation composition is an siloxane:

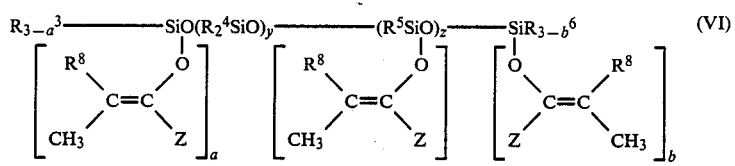

C. When the hydridosilane composition is an alkylalkoxysilane:

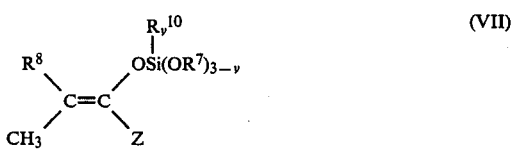

The O-silylated ketene acetals and enol ethers find utility as initiators for group transfer polymerization. Group-transfer polymerization is a method for the controlled formation of polymers from $\alpha, \beta$-unsaturated carbonyl compounds, i.e. esters, ketones, carboxamides, and nitriles via a sequential conjugate (Michael type) addition process. The technique employs silyl ketene acetals as initiators and is based on the known chemistry of the conjugate Michael addition of these silyl reagents to $\alpha, \beta$-unsaturated carbonyl compounds. This reaction has been extensively used in organic synthesis in recent years. The innovation contributed by DuPont scientists was the discovery of catalysts which promote the sequential conjugate addition of immediate silyl ketene acetals to $\alpha, \beta$-unsaturated carbonyl compounds, i.e. esters, ketones, carboxamides, or nitriles to form polymers.

The process is termed group-transfer polymerization because it proceeds via transfer of the silyl group from the initiator and each intermediate ketene acetal to the unsaturated hetero atom (e.g., carbonyl oxygen of an ester) of the next monomer molecule to be added to the polymer chain. Thus, the chain ends of all the intermediate molecules are reactive, i.e., the polymers are "living", and the reaction continues until all the $\alpha, \beta$-unsaturated carbonyl is consumed or the polymerization is terminated by addition of a reagent (e.g., a protic solvent) which cleaves the silyl group from the polymer molecule.

Group-transfer polymerization will be useful to control the molecular weight of acrylic polymers and thus may find utility in the production of acrylic automobile finishes and related products.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLE 1

A 100 ml 3-neck flask was equipped with a stirring bar, thermometer, 10 ml addition funnel and reflux condenser topped with a nitrogen inlet tube. The flask was charged with 15.7 g (0.07 mol) bis(trimethysilyloxy)methylsilane, 22.5 g xylene, 1.0 g phenothiazine and 200 ppm (23.64 mg) RhCl(PPh$_3$)$_3$. The solution was heated to reflux, at which time 7.1 g (0.07 mol) methyl methacrylate was added dropwise to the reaction over a period of 1-2 hours. The reaction was then cooled to room temperature and GC, GC/MS and NMR analyses confirmed the structure to be 1,1-dimethyl-2-methoxy-2-bis(trimethylsilyloxy)methylsiloxyethylene. The product was distilled at 58° C./40 mm Hg.

EXAMPLE 2

The reaction was run as described in Example 1 with the exception that methyl acrylate was used instead of methyl methacrylate. GC analysis showed that one major product had been formed. GC/MS and NMR confirmed the structure to be 1-methyl-2-methoxy-2-bis(trimethylsilyloxy)methylsiloxyethylene.

EXAMPLE 3

The reaction was run as described in Example 1 with the exception that the starting hydridosiloxane was heptamethylcyclotetrasiloxane instead of bis(trimethylsilyloxy)methylsilane. A single major product was formed in approximately 80% yield by GC analysis. GC/MS and NMR confirmed that this product was 1,1-dimethyl-2-methoxy-2-heptamethylcyclotetrasiloxyethylene.

EXAMPLE 4

A 100 ml 3-neck flask was equipped with a stirring bar, thermometer, 50 ml addition funnel and reflux condenser topped with a nitrogen inlet tube. The flask was charged with 15.0 g (0.112 mole), 1,1,3,3-tetramethyldisiloxane, 37.4 g xylene, 1.5 g phenothiazine and 200 ppm (22.2 mg) RhCl(PPh$_3$)$_3$. The solution was heated to reflux at which time 22.4 g (0.224 mol) methyl methacrylate was added dropwise to the reaction over a periodof 2-3 hours. The reaction was then cooled to room temperature and GC analysis showed that one major product was formed in greater than 90% yield. GC/MS and NMR confirmed that the structure of the product was 1,3-bis(1,1-dimethyl-2-methoxy-2-ethenoxy)-1,1,3,3-tetramethyldisiloxane.

EXAMPLE 5

A 250 ml 3-neck flask was equipped with a stirring bar, thermometer, 50 ml addition funnel and reflux condenser topped with a nitrogen inlet tube. The flask was charged with 30.9 g (0.15 mol) triisopropoxysilane, 45.9 g xylene, 1.82 g phenothiazine and 200 ppm (45.78 mg) RhCl(PPh$_3$)$_3$. The reaction was heated to reflux at which time 15.0 g (1.5 mol) methyl methacrylate was added dropwise to the reaction mixture over a period of 1-2 hours which was then heated an additional 5 hours. The reaction was then cooled to room temperature and GC analysis showed that one major product has been formed in greater than 80% yield. GC/MS and NMR confirmed the structure to be 1,1-dimethyl-2-methoxy- 2-triisopropoxysiloxyethylene. The product was distilled at 110° C./10 mm Hg.

EXAMPLE 6

The reaction was run as describe in Example 5 with the exception that tritertbutoxysilane was used as the starting silane instead of triisopropoxysilane. GC analysis showed that one major product has been formed in greater than 90% yield. GC/MS and NMR confirmed the structure to be 1,1-dimethyl-2-methoxy-2-tritertbutoxysiloxyethylene.

EXAMPLE 7

The reaction was run as described in Example 5 with the exception that triethoxysilane was used as the starting silane. GC analysis showed that two major products had been formed approximately in a 1 to 1 ratio. GC/MS and NMR confirmed that the structures were 1,1-dimethyl-2-methoxy-1-triethoxysiloxyethylene and methyl 2-methyl-3-triethoxysilylpropanoate.

EXAMPLE 8

The reaction was run as described in Example 5 with the exception that trimethoxysilane was used as the starting silane. GC analysis showed that two major products had been formed in approximately a 1 to 1 ratio. GC/MS and NMR confirmed that the structures were 1,1-dimethyl-2-methoxy-2-trimethoxysiloxyethylene and methyl 2-methyl-3-trimethoxysilylpropanoate.

EXAMPLE 9

A 100 ml 3-neck flask equipped with a stirring bar, thermometer, 10 ml addition funnel, and reflux condenser topped with a nitrogen inlet tube. The flask was charged with 7.0 g (0.028 mol) tritertbutoxysilane, 9.5 g xylene, 0.40 g phenothiazine and 200 ppm (10.37 mg) RhCl(PPh$_3$)$_3$. The solution was heated to reflux at which time 2.5 g (0.028 mol) methyl acrylate was added to the reaction mixture over a period of 1-2 hours which was then heated an additional 5 hours. The reaction was cooled to room temperature and GC analysis showed one major product had been formed in greater than 90% yield. GC/MS and NMR confirmed the structure to be 1-methyl-2-methoxy-2-tritertbutoxysiloxyethylene.

EXAMPLE 10

The reaction was run as described in Example 9 with the exception that triisopropoxysilane was used as the starting silane. GC/MS and NMR confirmed the structure of the product formed to be 1-methyl-2-methoxy-2-triisopropoxysiloxyethylene.

EXAMPLE 11

The reaction was run as described in Example 9 with the exception that rriethoxysilane was used as the starting silane. GC analysis showed that two major products had been formed. GC/MS and NMR confirmed the structures to be 1-methyl-2-methoxy-2-triethoxysiloxyethylene and methyl 3-triethoxysilylpropanoate.

EXAMPLE 12

The reaction was run as described in Example 9 with the exception that trimethoxysilane was used as the starting silane. GC analysis showed that two major products had been formed. GC/MS and NMR confirmed the structures to be 1-methyl-2-methoxy-2-trimethoxysiloxyethylene and methyl 3-trimethoxysilylpropanoate.

Comparative A

The reaction was run as described in Example 5 except that tritertbutoxysilane was used as the starting silane and H$_2$PtCl$_6$ (200 ppm) was used as the catalyst. After heating the reaction mixture for 8 hours at 150° C. no products were observed by GC.

Comparative B

The reaction was run as described in Example 13 except that H$_2$PtCl$_6$ (100 ppm) was used as the catalyst. After heating the reaction mixture for 8 hours at 150° C. no products had been formed.

EXAMPLE 13

A 50 ml 3-neck flask was equipped with a stirring bar, thermometer, 10 ml addition funnel and reflux condenser topped with a nitrogen inlet tube. The flask was charged with 4.7 g (0.029 mol) tris(dimethylamino)silane, 5.0 g xylene, 0.28 g phenothiazine and 200 ppm (8.32 mg) RhCl(PPh$_3$)$_3$. The solution was heated to reflux, at which time 2.5 g (0.029 mol) methyl acrylate was added dropwise to the reaction mixture over a period of 2 hours, which was then heated an additional 10 hours at 150° C. The reaction mixture was cooled to room temperature and GC analysis showed that one major product had been formed in greater than 80% yield. GC/MS and NMR confirmed the structure to be 1-methyl-2-methoxy-2-tris(dimethylamino)siloxyethylene.

EXAMPLE 14

A 1000 ml 3-neck flask was equipped with a stirring bar, thermometer, 250 ml addition funnel and reflux condenser topped with a nitrogen inlet tube. The flask was charged with 200 g (1.25 mol) tris(dimethylamino)silane, 307 g xylene, 12.0 g phenothiazine and 200 ppm (354 mg) RhCl(PPh$_3$)$_3$. The solution was heated to reflux, at which time 106.8 (1.24 mol) methyl acrylate was added dropwise to the reaction over a period of 2-3 hours which was then heated for an additional 10 hours at 150° C. The reaction mixture was then cooled to room temperature and GC analysis showed the formation of one major product in greater than 80% yield. This was then distilled at 140° C./20 mm Hg. GC/MS and NMR confirmed the structure to be 1-methyl-2-methoxy-2-tris(dimethylamino)siloxyethylene.

EXAMPLE 15

A 250 ml 3-neck flask was equipped with a stirring bar, thermometer, 50 ml addition funnel and reflux condenser topped with a nitrogen inlet tube. The flask was charged with 30 g (0.186 mole) tris(dimethylamino)silane, 50 g xylene, 0.02 g MEHQ and 200 ppm (44.4 mg) RhCl(PPh$_3$)$_3$. The solution was heated to reflux at which time 18.6 g (0.186 mol) methyl methacrylate was added dropwise to the reaction over a period of 1-2 hours, which was then heated an additional 8 hours at 150° C. The reaction mixture was cooled and GC showed that a single product had been formed in greater than 70% yield. GC/MS and NMR confirmed the structure to be 1,1-dimethyl-2-methoxy-2-tris(dimethylamino)siloxyethylene.

EXAMPLE 16

The reaction was run as described in Example 5 except that methyldiethoxysilane was used as the starting silane. GC analysis after the reaction was complete showed that two products had been formed in a approximately a 3 to 2 ratio. NMR and GC/MS confirmed that the structure of the major product was 1,1-dimethyl-2-methoxy-2-diethoxymethylsiloxyethylene and the minor product was methyl 2-methyl-3-diethoxymethylsilylpropanoate.

EXAMPLE 17

The reaction was run as described in Example 5 except that isobutylmethacrylate was used instead of methyl methacrylate. One major product was formed and NMR and GC/MS confirmed the structure to be 1,1-dimethyl-2-isobutoxy-2-triisopropoxysiloxyethylene.

EXAMPLE 18

The reaction was run as described in example 8 except that isobutylmethacrylate was used instead of methyl methacrylate. Two products were formed in a 2 to 1 ratio. The major one was determined by GC/MS and NMR to be 1,1-dimethyl-2-isobutoxy-2-trimethoxysiloxyethylene. The minor one was isobutyl 2-methyl-3-trimethoxysilylpropanoate.

EXAMPLE 19

The reaction was run as described in example 1 except that 2-trimethylsiloxyethylmethacrylate was used instead of methyl methacrylate. One major product was formed. GC/MS and NMR confirmed the structure to be 1,1-dimethyl-2-(2'-trimethylsiloxyethoxy)-2-bis(-trimethylsilyloxy)methylsiloxyethylene.

EXAMPLE 20

The reaction was run as described in Example 15 except that dimethylaminodimethylsilane was used instead of tris(dimethylamino)silane. One major product was formed and NMR and GC/MS confirmed the structure to be 1,1-dimethyl-2-methoxy-2-dimethylaminodimethylsiloxyethylene.

EXAMPLE 21

The reaction was run as described in Example 15 except that methylbis(dimethylamino)silane was used instead of tris(dimethylamino)silane. One major product was formed and NMR and GC/MS confirmed the structure to be 1,1-dimethyl-2-methoxy-2-methyl bis(-dimethylamino)siloxyethylene.

EXAMPLE 22

The reaction was run as described in example 5 except that dimethylethoxysilane was used as the starting silane. Two products were formed in a ratio of 3 to 1. The structure of the major product was confirmed by GC/MS and NMR to be 1,1-dimethyl-2-methoxy-2-dimethylethoxysiloxyethylene.

EXAMPLE 23

A sample of 1,1-dimethyl-2-methoxy-2-triethoxysiloxyethylene prepared as described in Example 7 was used as an initiator for Group Transfer Polymerization. The procedure followed was identical to that described in the *Journal of the American Chemical Society*, Vol. 105, page 5706, with the only exception being that 1,1-dimethyl-2-methoxy-2-triethoxysiloxyethylene was used instead of 1-methoxy-1-(trimethylsiloxy)-2-methyl-1-propene. Group Transfer Polymerization did occur.

EXAMPLE 24

A sample of 1,1-dimethyl-2-methoxy-2-bis(trimethylsilyloxy)methylsiloxyethylene prepared as described in Example 1 was used as an initiator for Group Transfer Polymerization. The procedure followed was identical to that described in the *Journal of the American Chemical Society*, Vol. 105, page 5706, with the only exception being that 1,1-dimethyl-2-methoxy-2-bis(trimethylsilyloxy)-methylsiloxyethylene was used instead of 1-methoxy-1-(trimethylsiloxy)-2-methyl-1-propene. Group Transfer Polymerization did occur.

EXAMPLE 25

A sample of 1,1-dimethyl-2-methoxy-2-methyl bis(-dimethylamino)siloxyethylene prepared as described in Example 21 was used as an initiator for Group Transfer Polymerization. The procedure followed was identical to that described in the *Journal of the American Chemical Society*, Vol. 105, pge 5706, with the only exception being that 1,1-dimethyl-2-methoxy-2-methylbis(dimethylamino)siloxyethylene was used instead of 1-methoxy-1-(trimethylsiloxy)-2-methyl-1-propene. Group Transfer Polymerization did occur.

EXAMPLE 26

A sample of 1,1-dimethyl-2-methoxy-2-methydiethoxysiloxy-ethylene prepared as described in Example 16 was used as an initiator for Group Transfer Polymerization. The procedure followed was identical to that described in the *Journal of the American Chemical Society*, Vol. 105, page 5706, with the only exception being that 1,1-dimethyl-2-methoxy-2-methyldiethoxy-siloxyethylene was used instead of 1-methoxy-1-(trimethylsiloxy)-2-methyl-1-propene. Group Transfer Polymerization did occur.

EXAMPLE 27

A sample of 1,1-dimethyl-2-methoxy-2-dimethylaminodimethylsiloxyethylene prepared as described in Example 20 was used as an initiator for Group Transfer Polymerization. The procedure followed was identical to that described in the *Journal of American Chemical Society*, Vol. 105, page 5706, with the only exception being that 1,1-dimethyl-1-methoxy-2-dimethylaminodimethylsiloxy-ethylene was used instead of 1-methoxy-1-(trimethylsiloy)-2-methyl-1-propene. Group Transfer Polymerization did occur.

EXAMPLE 28

A 250 ml 3-neck flask was equipped with a stirring bar, thermometer, 50 ml addition funnel and reflux condenser topped with a nitrogen inlet tube. The flask was changed with 48 g (0.714 mol) of methyldiethoxysilane, 25 g of triisopropylbenzene, 0.32 g monomethyl hydroquinone and 300 ppm (0.129 g) $RhCl(PPh_3)_3$. The solution was heated at 80° C. at which time 25 g (0.357 mol) of methylvinylketone was added over a period of 1–2 hours. The reaction was exothermic and during the course of the addition of methylvinylketone the reaction temperature increased to 160° C. The reaction was cooled to room temperature and GC analysis showed that one major product had been formed. GC/MS confirmed that the major product was a mixture of the cis and trans isomers of 3-(methyldiethoxysiloxy)but-2-ene.

EXAMPLE 29

The reaction was run as described in Example 28 with the exception that dimethylethoxysilane was used as the starting silane. GC analysis showed one major product had been formed, which GS/MS confirmed was a mixture of the cis and trans isomers of 3-(dimethylethoxysiloxy)but-2-ene.

EXAMPLE 30

The reaction was run as described in Example 28 with the exception that triethoxysilane was used as the starting silane. GC analysis showed the formation of one major product which GC/MS confirmed to be a mixture of cis and trans 3-(triethoxysiloxy)but-2-ene.

EXAMPLE 31

A 500 ml 3-neck flask was equipped with a stirring bar, thermometer, 100 ml addition funnel and reflux condenser topped with a nitrogen inlet tube. The flask was charged with 145 g (0.71 mol) tris(dimethylamino)silane, 115 g xylene, 0.33 g monomethyl hydroquinone and 300 ppm (0.31 g) RhCl(PPh$_3$)$_3$. The solution was heated to 95° C., at which time 50 g (0.71 mol) methylvinylketone was added dropwise over a period of 1-2 hours. There was an initial exotherm which increased the temperature to 140° C. After the addition was complete the reaction was cooled to room temperature and GC analysis showed one major product had been formed. GC/MS confirmed that the major product was a mixture of cis and trans 3-(tris(dimethylamino)siloxy)but-2-ene.

EXAMPLE 32

The reaction was run as described in Example 31 with the exception that methylbis(dimethylamino)silane was used as the starting silane and triisopropylbenzene was used as the solvent. GC/MS confirmed that the single product formed was a mixture of cis and trans 3-(methylbis(dimethylamino)siloxy)but-2-ene.

EXAMPLE 33

A 500 ml 3-neck flask was equipped with a stirring bar, thermometer, 100 ml addition funnel and reflux condenser topped with a nitrogen inlet tube. The flask was charged with 158 g (0.714 mol) bis(trimethylsiloxy)methylsilane, 150 g xylene, 0.42 g monomethyl hydroquinone and 300 ppm (0.43 g) RhCl(PPh$_3$)$_3$. The solution was heated to 80° C. at which time 50 g (0.714 mol) methylvinylketone was added over a period of one to two hours. There was an initial exotherm and the reaction temperature increased to 140° C. After the addition was complete, the reaction was cooled to room temperature and GC analysis showed one major product had been formed in greater than 90% yield. GC/MS confirmed that this product was a mixture of cis and trans 3-(bis(trimlethylsiloxy)methylsiloxy)but-2-ene.

EXAMPLE 34

A sample of 1,1-dimethyl-2-methoxy-2-dimethylethoxy-siloxyethylene prepared as described in Example 22 was used as an initiator for Group Transfer Polymerization. The procedure followed was identical to that described in the *Journal of the American Chemical Society*, Vol. 105, page 5706, with the only exception being that 1,1-dimethyl-2-methoxy-2-dimethylethoxysiloxyethylene was used instead of 1-methoxy-1-(trimethylsiloxy)-2-methyl-1-propene. Group Transfer Polymerization did occur.

We claim:

1. A O-silylated ketene acetal or enol ether selected from the group of O-silylated ketene acetals and enol ethers consisting essentially of:

(a) O-aminosilylated ketene acetals and enol ethers of the general formula:

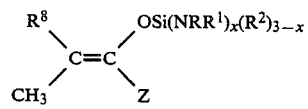

(b) O-siloxanesilylated ketene acetals and enol ethers of the general formulae:

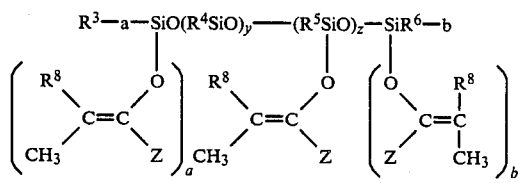

(c) O-alkoxysilylated ketene acetals of the general formula:

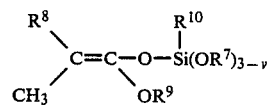

wherein R, R$^1$, and R$^2$ are individually alkyl or aryl group containing 1 to 8 carbon atoms and R can be hydrogen; R$^3$, R$^4$, R$^5$, R$^6$, R$^7$, and R$^{10}$ are individually alkyl groups containing 1 to 8 carbon atoms; R$^8$ is hydrogen or an alkyl or aryl groups having 1 to 8 carbon atoms; R$^9$ are individually alkyl or aryl groups having 1 to 8 carbon atoms; Z is selected from the group consisting of hydrogen, an alkyl group, an aryl group, an alkoxy group and an aryloxy group containing from one to fifteen carbon atoms and a has a value of 0 or 1, b has a value of 0 or 1, y has a value from 1 to 500, z has a value from 0 to 499, and, the sum of y+z equals from 1 to 500 with the proviso that if z is 0, a+b must equal at least one; x has a value of 1, 2 or 3; and v has a value of 0, 1 or 2.

2. The O-silylated ketene acetal and enol ether of claim 1 wherein R, R$^1$ and R$^2$ are individually methyl ethyl or phenyl groups and x has a value of 3.

3. The O-silylated ketene acetal and enol ether of claim 1 wherein R, R$^1$, R$^2$, R$^3$, R$^4$, R$^5$, R$^6$, R$^7$, and R$^{10}$ are methyl groups.

4. The O-silylated ketene acetal and enol ether of claim 1 wherein v is 0.

5. 1,1-dimethyl-2-methoxy-2-bis(trimethylsilyloxy)methylsiloxyethylene.

6. 1-methyl-2-methoxy-2-bis(trimethylsilyloxy)methylsiloxyethylene.

7. 1,1-dimethyl-2-methoxy-2-heptamethylcyclotetrasiloxyethylene.

8. 1,3-bis(1,1-dimethyl-2-methoxy-2-ethenoxy)-1,1,3,3-tetramethyldisiloxane.

9. 1,1-dimethyl-2-methoxy-2-triisopropoxysiloxyethylene.

10. 1,1-dimethyl-2-methoxy-2-tritertbutoxysiloxyethylene.

11. 1,1-dimethyl-2-methoxy-1-triethoxysiloxyethylene.

12. 1-methyl-2-methoxy-2-tritertbutoxysiloxyethylene.

13. 1-methyl-2-methoxy-2-triisopropoxysiloxyethylene.

14. 1-methyl-2-methoxy-2-tris(dimethylamino)siloxyethylene.

15. 1,1-dimethyl-2-methoxy-2-tris(dimethylamino)siloxyethylene.

16. A process for preparing O-silylated ketene acetals and enolethers which comprises a 1,4-hydrosilation of a hydrosilation composition selected from the group consisting of:

(a) aminosilanes of the formula:

$$H-Si(NRR^1)_x(R^2)_{3-x};$$

(b) siloxanes of the formula:

$$R_{3-a}(H)_a SiO(R_2SiO)_y(R^5SiO)_z Si(H)_b R_{3-b};$$

and (c) alkoxysilanes of the formula:

$$H-Si(OR^7)_{3-v}^{R_v}$$

with an $\alpha,\beta$-unsaturated carbonyl compound of the formula:

$$CH_2=C-C\begin{matrix}R^8\\|\\OR^9\end{matrix}\begin{matrix}O\\\diagup\diagdown\end{matrix}$$

in the presence of a rhodium catalyst wherein R, $R^1$, and $R^2$ are individually alkyl or aryl group containing 1 to 8 carbon atoms and R can be hydrogen; $R^3$, $R^4$, $R^5$, $R^6$, $R^7$, and $R^{10}$ are individually alkyl groups containing 1 to 8 carbon atoms; $R^8$ is hydrogen or an alkyl or aryl groups having 1 to 8 carbon atoms; $R^9$ are individually alkyl or aryl groups having 1 to 8 carbon atoms; Z is selected from the group consisting of hydrogen, an alkyl group, an aryl group, an alkoxy group and an aryloxy group containing from one to fifteen carbon atoms and a has a value of 0 or 1, b has a value of 0 or 1, y has a value from 1 to 500, z has a value from 0 to 499, and, the sum of y+z equals from 1 to 500 with the proviso that if z is 0, a+b must equal at least one; x has a value of 1, 2 or 3; and v has a value of 0, 1 or 2.

17. The process of claim 16 wherein the catalyst concentration is 0.00001 to 0.05 mole percent based on the hydrosilation composition.

18. The process of claim 16 wherein the hydrosilation occurs at a temperature greater than 40° C.

19. The process of claim 18 wherein the temperature is 70° to 150° C.

20. The process of claim 16 wherein a solvent is employed.

21. 1,1-dimethyl-2-methoxy-2-methyldiethoxysiloxyethylene.

22. 1,1-dimethyl-2-methoxy-2-dimethylaminodimethylsiloxyethylene.

23. 1,1-dimethyl-2-methoxy-2-methyl bis (dimethylamino)siloxyethylene.

24. 1,1-dimethyl-2-methoxy-2-dimethylethoxysiloxyethylene.

* * * * *